United States Patent [19]

Mathason

[11] 4,262,024

[45] Apr. 14, 1981

[54] METHOD FOR TESTING BAKING STRENGTH OF FLOUR

[76] Inventor: Irwin J. Mathason, 6659 Sanzo Rd., Baltimore, Md. 21209

[21] Appl. No.: 71,517

[22] Filed: Aug. 31, 1979

[51] Int. Cl.$^3$ ............................................. A21D 2/02
[52] U.S. Cl. ................................. 426/231; 426/233; 73/169
[58] Field of Search ................... 426/231, 233; 73/169

[56] References Cited

PUBLICATIONS

Reprint from Cereal Chemistry AACC 1957, vol. 34. #1, U.S.A.. Pinckney et al "Further Developments in the Sedimentation Test for Wheat Quality" pp. 16–25.
U.S. Department of Agriculture, Office of Information Photo Series #59, Oct. 1961, "Making The Sedimentation Test for Bread Baking Quality of Wheat".
The Baker's Digest, Aug. 1978, pp. 20–23, Bernardin "Gluten Protein Interaction with Small Molecules and Ions-the Control of Flour Properties".
Cereal Food World vol. 23 #7, Jul. 78, pp. 374–375, Neukom et al, "Oxidative Gelation of Wheat Flour Pentosans:A New Way of Cross Linking Polymers".
Pyler, Baking Science & Technology. vol. 1 Siebel publishing Co. Chicago, Ill., 1974, pp. 347–350.
Matz, Bakery Technology and Engineering. Avi Publishing Co. Inc. Westport, Conn., 1973, pp. 12–18.
Olcott et al. "Specific Group Reagents for Proteins" Chemical Reviews, vol. 41, No. 1, 8/47, pp. 171–187.
Jackel, Bakery, Jan. 1980, p. 117.
Mathason, Bakers Digest, Apr. 1980, vol. 54, No. 2 pp. 22–24.

Primary Examiner—Joseph M. Golian
Assistant Examiner—Elizabeth A. Hatcher
Attorney, Agent, or Firm—Lawrence I. Field

[57] ABSTRACT

A procedure is described for determining the overall performance of a flour in baked goods, i.e. for determining the baking strength of the flour so that a baker may compensate for the same when preparing baked goods with the flour.

3 Claims, No Drawings

METHOD FOR TESTING BAKING STRENGTH OF FLOUR

This invention relates to methods and apparatus for determining the total performance of a flour in baked goods.

Individuals involved in the commercial preparation of baked products such as bread, rolls, cakes and pastries are often faced with the problems created by the uneven performance of the wheat flour or rye flour utilized in the preparation of such goods.

Although a number of tests have been developed for measuring the rheological properties of flour-water mixtures and other tests have been developed for the measurement of physical properties such as density or particle size or whiteness, none of such tests has been found to accurately reflect or forecast the baking strength of the flour, i.e. the final loaf volume, oven expansion and other variables in a baking process, or to provide information which the baker can utilize to alter his recipe or handling schedule so as to produce a product with desired configuration and other characteristics which make it acceptable to a consumer.

The present invention is directed to means for providing such information to a baker.

This invention is related to a chemical method and related measuring devices for determining the baking strength of flour. More specifically this is accomplished through observance of the characteristics of gels formed by chemically induced oxidative gelation of flour-wheat mixtures heated to temperatures in the range below the normal flour-starch gelatinization temperature, e.g. in the range 100° F. to 130° F.

In the past mechanisms have been developed for estimating rheological properties of flour-water mixtures, e.g. through measurement of torque and/or energy input. Other mechanisms have been developed which measure gelatinization characteristics of flours, and there exists a chemical means of measuring protein precipitates formed by treatment with lactic acid to estimate the quantity and strength of the protein. While all of the previous methods supply useful information, none give a clear cut aggregate estimation of the likelihood that a given flour sample will produce satisfactory bread in terms of the final characteristics as generally understood by the baking industry and sought after by consumers of baking products.

Hence there exists a need for a simple, rapid, easily conducted test for use by researchers interested in creating new strains of grains for optimum utilization, and for use by millers to control processing and blending of grains, and for use by bakers to write specifications for flour likely to give best shop performance and to make processing adjustments to compensate for flour quality variances.

The flour test of the present invention measures the ability of the flour under test to produce well formed loaves of bread or units of rolls and other related yeast raised products.

Briefly the method of the invention comprises: (1) preparation of a flour-water mixture; (2) addition of a minute amount of an oxidizing agent to the mixture; (3) addition of a source of small ions to the mixture; (4) gentle heating of the resulting composition to a temperature below the normal gelatinization temperature, i.e. the temperature at which the starch in the flour normally forms a gel; (5) observation and measurement of at least one physical property of the heated mixture, by physical, chemical or optical means; (6) comparison of the measured values with values obtained by similarly processing a flour of known baking strength; and (7) adjustment of the mixture to be baked to compensate for the departure of the strength of the flour tested, from the norm.

The invention will be better understood from the description which follows, in which preferred embodiments are set forth in accordance with the Patent Statutes, by way of illustration and not intended to be limiting.

(1) THE FLOUR

The present invention is applicable to wheat flour, rye flour and similar flours including those which have been chemically bleached. It is intended primarily as an aid to commercial bakers and hence is particularly applicable to the testing of wheat flour and rye flour.

(2) THE OXIDIZING AGENT

Oxidative gelation of wheat flour pentosans has been described in the literature, e.g. in Cereal Foods World Vol. 23 No. 7 July 1978, pages 374–376. Any of the known oxidizing agents listed in that article or others of a similar nature may be used in the practice of the present invention, including the following:

Hydrogen peroxide/peroxidase;
Sodium chlorite ($NaClO_2$);
Ferric chloride;
Potassium ferricyanide;
Potassium periodate;
Iodine;
Potassium permanganate; and
Linoleic acid/lipoxygenase.

(3) THE SMALL ION OR MOLECULE

The interaction of gluten protein with small molecules and ions has been reported in The Bakers Digest, August 1978, pages 133 and 134 wherein the specific effects brought about by ions which appear to bind on the protein surface is discussed.

The preferred small ions are the monovalent cations $K^+$, $Na^+$, $H^+$, and $NH_4^+$ and the preferred source of small ions in the present invention is KCl, but other small ion sources which give similar results include $KBrO_3$, $KIO_3$, potassium maleate, cysteine, potassium fumurate, potassium phytate, ascorbic acid, sodium dodecyl sulfate, cetyl trimethyl ammonium bromide, gulonic acid and stearic acid, or the sodium salts of any of the foregoing.

(4) THE PROPERTIES TO BE MEASURED

The oxidative gelation of a flour-water mixture affects the physical properties of the mixture in any of several ways. By suitable means, changes in the optical, chemical or physical properties can be observed and measured and the results can be correlated in order to permit the baker to alter his shop practice or his recipe in order to produce a baked product with desired properties.

(5) EXAMPLES

In the examples which follow the oxidizing agent utilized is iodine and the additive is KCl and a change in color is observed, this being the preferred procedure, but other oxidizing agents and small ion sources may be used which do not give a color change, in which case other physical properties such as viscosity change, or opacity change may be measured and compared with standards established by tests performed on flours which have been determined as possessing good baking characteristics.

In its simplest form the preferred method used to implement the test of the present invention is as follows:

A weighed amount of the flour under test is mixed in a glass beaker wit an appropriate volume of water at a temperature of between about 65° F. and 75° F. The temperature is not critical but water which is too cold does not function as well as water in the indicated temperature range and warmer water may obscure the effect of the subsequent heating described below.

A small amount of a dilute aqueous solution of iodine and a small amount of a saturated solution of KCl are added to the water-starch mixture, whereupon a blue color appears. The resulting solution is stirred vigorously and is heated gently. As the temperature rises the blue color fades and disappears.

End point is taken at the point where no blue color is visible and requires approximately five minutes. The temperature observed at the end point is usually somewhere between 110° F. and 130° F. At the end point, heating is discontinued and the beaker containing flour, water and reagents is permitted to stand undisturbed. Within approximately ten minutes a precipitate forms and the number of ml of precipitate is read. Both values are noted—temperature at end point and precipitate volume.

Wheat flours of poorer baking quality wherein the flours contain comparable amounts of protein give lower end point temperatures and lower precipitate volumes while wheat flours of good baking quality give higher end point temperatures and larger precipitate volumes.

Tables I-VI set forth results obtained using the proportions in the following example.

Three gms of flour were mixed with 30 gms of water in a 50 ml beaker. Initial water temperature was 65° to 75° F. One ml of a solution of 1/10% iodine in water was introduced into the beaker along with 1 ml of a saturated potassium chloride (KCl) solution. Upon addition of iodine solution a blue color appears. The resulting mixture was stirred rapidly and gently heated. As the temperature rose the blue color began to fade. The end point and subsequent precipitate formation are determined as described above.

Wheat flours with higher protein content tend to give lower end point temperatures and lower precipitate volumes.

TABLE I

Pastry flour (8.5% protein) to which varying percentages of vital wheat gluten (VWG) had been added.

|  | End Point Temperature °F. | Volume of Precipitate |
|---|---|---|
| Pastry flour + 0% VWG 83% Protein | 128° | 8ml |
| Pastry flour + 8% VWG 83% Protein | 124° | 8ml |
| Pastry flour + 12% VWG | 120° | 8ml |
| Pastry flour + 16% VWG | 116° | 8ml |

Table II shows the typical values obtained with flours of known good baking quality and known poorer baking quality.

TABLE II

| Flour | GOOD QUALITY | | POORER QUALITY | |
|---|---|---|---|---|
|  | End Point Temp. | Volume of Precip. | End Point Temp. | Volume of Precip. |
| Patent (12% Protein) | 120° F. | 12 ml | 110° F. | 9 ml |
| High Gluten (14% Protein) | 122° F. | 12 ml | 116° F. | 10 ml |
| Clear (14.8% Protein) | 120° F. | 12 ml | 112° F. | 10 ml |

It has been found that a wheat flour which has been subjected to additional milling shows lower end point temperature and smaller precipitate volumes than did the original flour. This is shown in Table III.

TABLE III

|  | End Point Temperature | Volume of Precipitate |
|---|---|---|
| Patent (normal milling) | 124° F. | 12 ml |
| Patent (given additional milling) | 116° F. | 9 ml |

Wheat flour to which purified pentosan extract has been added shows higher end point temperature and precipitation value than did the original flour, as shown in Table IV.

TABLE IV

|  | End Point Temperature | Volume of Precipitate |
|---|---|---|
| High gluten flour + 0% pentosan | 122° F. | 12 ml |
| High gluten flour + 0.25% pentosan | 134° F. | 18 ml |
| High gluten flour + 0.50% pentosan | 138° F. | 20 ml |
| High gluten flour + 1.50% pentosan | 138° F. | 24 ml |
| High gluten flour + 2.00% pentosan | 152° F. | (Formed solid gel with no precipitate) |

Chlorine treated cake flours showed unusually high end point temperatures and precipitate volumes as shown in Table V.

TABLE V

| End Point Temperature | 140° F. |
|---|---|
| Precipitate Volume | 30 ml |
| pH | 4.5 |

Rye flour which has been in storage for an extended period gives higher end point values than rye flour which has not had extended storage time. Rye bread made from flours stored too long will develop cracks in the crust surface.

TABLE VI

|  | End Point Temperature | Volume of Precipitate |
|---|---|---|
| Rye flour (acceptable storage time) | 106° F. | 14 ml |
| Rye flour (excessive storage time) | 124° F. | 28 ml |

One possible explanation for the foregoing observations concerning wheat flour may be the known mechanisms of oxidative gelation of proteins and pentosans and the aggregation of wheat proteins induced by small ions such as potassiom chloride. As discussed in the above noted literature, oxidative gelation can occur between protein and ferulic acid containing pentosans and can occur between proteins through formation of ditryosine cross links in proteins by oxidative phenolic coupling of tryosine residues.

Iodine solution is an oxidizing agent capable of producing such gelation. Iodine gives the test method a visible property. Strength of the gel formed is another method of evaluation. Other compounds which are known to cause such gelation and can be used in the method of the present invention include hydrogen peroxide/peroxidase, linoleic acid/lipoxygenase, sodium chlorite ($NaCl_2$), potassium periodate, ferric chloride, potassium ferricyanide and other compounds of similar nature.

Aggregation of wheat proteins is caused by reaction with potassium chloride. Such aggregates are thought to have an effect upon the viscoelastic properties of wheat protein. When KCl solution was added to 1/10% iodine solution, it was found that the same wheat flour sample gave higher end point temperatures and higher precipitate volumes than with the iodine solution alone. Other reagents which can be used in the method of this invention include the potassium or sodium salts of gluconic acid, stearic acid, $HBrO_3$, $HIO_3$, ascorbic acid, maleic acid, fumaric acid and sodium dodecyl sulphate and cetylitrimethyl ammonium bromate.

Instead of iodine which produces a visible color change, any of the other indicated oxidizing agents may be used in the process. When this is done the viscosity of the mixture is measured during the oxidative gelation process and the changes are correlated to the viscosity of mixture made from flours known to have good baking qualities.

Other methods of carrying out the process include the use of optical devices to follow the changes in color (when iodine is used) or to follow the changes in opacity (when other oxidants are used).

On the basis of the test results obtained, a baker would add gluten, or alter his recipe in other ways, or he might alter his baking temperature or time or otherwise alter his shop practice, e.g. by increasing mixing time, or formula water, or by decreasing the amount of vital wheat gluten. The amount of oxidizing agent added may be diminished and the protease addition would be increased to compensate for stronger flour, and the converse adjustments are made for flours whose test shows a weaker baking strength. It will be noted that the adjustments for stronger flour result in a cost reduction. Dough weight could be reduced to maintain equal finished product volume using stronger flour which gives a further cost reduction, or a bigger unit could be made at the same weight for sales appeal. The converse set of weight adjustments are necessary with weaker flour resulting in higher cost.

Having now described preferred embodiments of my invention in accordance with the Patent Statutes it is not intended that it be limited except as may be required by the appended claims.

I claim:

1. A method of testing the baking strength of a flour which comprises:
   (a) preparing a mixture of said flour and water;
   (b) adding a small amount of a source of small ions selected from the group consisting of $K^+$, $Na^+$, $H^+$ and $NH_4^+$ to said mixture;
   (c) thereafter adding a small amount of an oxidizing agent to the resulting mixture to form a colored reaction product in the resulting composition;
   (d) gently heating the resulting composition to a temperature below the gelatinization temperature of said composition;
   (e) observing the disappearance of color and the temperature at which this occurs in said composition and the opacity of said composition;
   (f) discontinuing the gentle heating of said composition and thereafter observing the volume of precipitate which forms after said gentle heating its discontinued and the color has disappeared from said composition;
   (g) comparing said observations with corresponding observations of a flour of known baking strength; and
   (h) adjusting a mixture to be baked with said flour in accordance with the results of said comparison.

2. The process of claim 1 wherein the oxidizing agent is iodine and the source of small ions is KCl.

3. The process of claim 1 wherein the adjustment of recipe includes addition of gluten to flour found to have weak baking strength and deletion or reduction of gluten from flour showing greater baking strength than those in prior use.

* * * * *